(12) United States Patent
Wolfe

(10) Patent No.: US 9,216,299 B2
(45) Date of Patent: Dec. 22, 2015

(54) ELECTROMAGNETIC PATHOLOGIC LESION TREATMENT SYSTEM AND METHOD

(76) Inventor: Thomas J. Wolfe, Redlands, CA (US)

(*) Notice: Subject to any disclaimer, the term of this patent is extended or adjusted under 35 U.S.C. 154(b) by 650 days.

(21) Appl. No.: 13/443,367

(22) Filed: Apr. 10, 2012

(65) Prior Publication Data

US 2012/0239022 A1 Sep. 20, 2012

Related U.S. Application Data

(63) Continuation-in-part of application No. PCT/US2010/053409, filed on Oct. 20, 2010.

(60) Provisional application No. 61/253,705, filed on Oct. 21, 2009.

(51) Int. Cl.
*A61N 1/40* (2006.01)
*A61B 17/22* (2006.01)
*A61M 25/09* (2006.01)
(Continued)

(52) U.S. Cl.
CPC . *A61N 1/40* (2013.01); *A61B 17/22* (2013.01); *A61M 25/0082* (2013.01); *A61M 25/0158* (2013.01); *A61M 25/09* (2013.01); *A61N 2/02* (2013.01); *A61B 18/04* (2013.01); *A61B 2017/00876* (2013.01); *A61B 2017/22038* (2013.01); *A61B 2017/22042* (2013.01); *A61B 2017/22079* (2013.01); *A61B 2017/22082* (2013.01); *A61M 25/00* (2013.01); *A61M 25/0054* (2013.01); *A61M 25/0108* (2013.01); *A61M 2025/0008* (2013.01); *A61M 2025/09133* (2013.01); *A61M 2025/09183* (2013.01)

(58) Field of Classification Search
CPC .............. A61M 25/0082; A61M 25/0147; A61M 25/0158; A61M 25/09; A61M 29/00; A61B 17/12022; A61B 17/12113; A61B 17/12145; A61B 17/1214; A61B 17/1215; A61B 17/22; A61B 18/18; A61B 2018/00404; A61N 1/40
USPC .................................. 606/32, 33, 41
See application file for complete search history.

(56) References Cited

U.S. PATENT DOCUMENTS

| 4,846,193 A | 7/1989 | Tremulis et al. |
| 5,643,254 A | 7/1997 | Scheldrup et al. |

(Continued)

FOREIGN PATENT DOCUMENTS

| WO | WO 2006/074510 A1 | 7/2006 |
| WO | WO 2011/050085 | 4/2011 |

OTHER PUBLICATIONS

Wentworth, Stuart M. "Fundamentals of Electromagnetics with Engineering Applications". John Wiley and Sons, Inc., 2005. pp. 146, 465.*

(Continued)

*Primary Examiner* — Allen Porter, Jr.
(74) *Attorney, Agent, or Firm* — Foley & Lardner LLP

(57) ABSTRACT

A method of treating a pathologic legion, such as an intravascular thrombus, is disclosed. The method comprises providing a guide wire and catheter with at least one inductive element within a blood vessel to a distal location associated with the pathologic lesion; and providing electromagnetic energy via at least one inductive element to the pathologic lesion to cause thrombolysis. Medicated magnetic particles can be endovascularly localized and concentrated to the vascular territory affected by the pathologic lesion.

15 Claims, 11 Drawing Sheets

(51) Int. Cl.
*A61N 2/02* (2006.01)
*A61B 17/00* (2006.01)
*A61M 25/00* (2006.01)
*A61M 25/01* (2006.01)
*A61B 18/04* (2006.01)

(56) References Cited

U.S. PATENT DOCUMENTS

| | | | |
|---|---|---|---|
| 5,743,905 | A | 4/1998 | Eder et al. |
| 5,895,385 | A | 4/1999 | Guglielmi et al. |
| 5,976,131 | A * | 11/1999 | Guglielmi et al. ............. 606/49 |
| 6,569,151 | B1 | 5/2003 | Nash et al. |
| 6,613,002 | B1 | 9/2003 | Clark et al. |
| 6,878,151 | B2 | 4/2005 | Carrison et al. |
| 2002/0091421 | A1* | 7/2002 | Greenberg et al. ............. 607/54 |
| 2002/0095084 | A1 | 7/2002 | Vrijheid et al. |
| 2003/0074034 | A1* | 4/2003 | Penner et al. .................. 607/59 |
| 2003/0083726 | A1* | 5/2003 | Zeijlemaker et al. ......... 607/122 |
| 2003/0100848 | A1 | 5/2003 | Gosiengfiao et al. |
| 2003/0236533 | A1 | 12/2003 | Wilson et al. |
| 2004/0039417 | A1* | 2/2004 | Soykan et al. .................... 607/2 |
| 2004/0236344 | A1 | 11/2004 | Monstadt et al. |
| 2006/0089637 | A1 | 4/2006 | Werneth et al. |
| 2006/0142632 | A1* | 6/2006 | Meretei .......................... 600/12 |
| 2006/0282110 | A1 | 12/2006 | Litvack et al. |
| 2008/0262489 | A1* | 10/2008 | Steinke .......................... 606/33 |
| 2008/0294181 | A1 | 11/2008 | Wensel et al. |
| 2009/0054918 | A1 | 2/2009 | Henson |
| 2010/0004528 | A1 | 1/2010 | Weiss et al. |
| 2011/0098559 | A1 | 4/2011 | Besz et al. |

OTHER PUBLICATIONS

International Search Report and Written Opinion for Application No. PCT/US2010/053409, mail date Jun. 29, 2011, 12 pages.
Extended European Search Report and Search Opinion for corresponding EP Application No. 10825609.0 dated Mar. 12, 2013, 11 pages.
International Search Report and Written Opinion for Application No. PCT/US2013/035815/, mail date Jul. 18, 2013, 13 pages.
International Preliminary Report on Patentability for PCT application No. PCT/US2013/035815, mail date Oct. 23, 2014, 8 pages.

* cited by examiner

ELECTROMAGNETIC PATHOLOGIC LESION TREATMENT SYSTEM AND METHOD

CROSS-REFERENCE TO RELATED APPLICATIONS

The present application is a continuation-in-part of PCT/US2010/053409 which claims the benefit of and priority to U.S. Provisional Application No. 61/253,705, filed on Oct. 21, 2009, including the specification, drawings, claims and abstract, which is incorporated herein by reference in its entirety.

FIELD

The present specification relates generally to an apparatus for and method of facilitating the dissolution of a pathologic lesion (e.g., a thrombus) in a blood vessel. More particularly, the specification relates to an apparatus for and method of providing electromagnetic energy in close proximity to a distally located pathologic lesion to aid in the treatment of the thrombus.

BACKGROUND

Blood flow through the circulatory system can be restricted when a thrombus (blood clot) develops inside a blood vessel or when an occlusive thromboembolism occurs. A thrombus is generally formed from platelets and fibrin to prevent loss of blood due to an injury to the blood vessel or bodily tissue. A thrombus may also form directly on an atherosclerotic lesion within a blood vessel and lead to thrombotic occlusion in situ. Serious complications can occur if a thrombus grows too large and obstructs too much of the blood vessel. The thrombus may also break loose, forming an embolus that can lodge in another part of the body or distal vasculature, obstructing blood flow and potentially causing irreversible harm to organs or death.

Ischemia is a reduction in blood flow to an organ or tissue, causing damage due to a lack of sufficient oxygen or fuel being delivered to the cells. One type of stroke (an ischemic stroke) occurs when a cerebral vessel is obstructed (such as by a thrombus or an embolus), reducing blood flow to a specific region of the brain. A blockage of this type can quickly lead to irreversible damage to brain tissue and death. It can be seen, therefore, that there is a great need for effective treatment options to dissolve or otherwise remove/reduce blood clots to increase the blood flow to organs such as the brain and to resolve any thrombus which occurs in situ or breaks loose to cause an embolism.

Thrombolysis and fibrinolysis (the break-up or dissolution of a blood clot) generally involves the use of thrombolytic and fibrinolytic drugs. The drugs activate an enzyme which breaks down the protein holding the clot together, making the clot soluble and less durable. The treated clot is then broken up and removed from the blood vessel either mechanically or through natural physiologic processes. These medications can be delivered with intravenous and intra-arterial injections.

Data has been emerging regarding the use of exogenous application of different forms of energy to assist in thrombolysis. One such application energy is the combined dissolving of thrombus in brain ischemia using transcranial ultrasound and systemic tissue plasminogen activator (CLOTBUST trial; J Neuroimaging: 14 (2): 108-112). Such a treatment involves the external application of diagnostic ultrasound along with the use of a tissue plasminogen activator (tPA) protein to accelerate flow improvement and achieve faster and more complete resolution of the thrombus. Other treatments include the use of lasers or ultrasound (US) catheters positioned endovascularly adjacent to the affected area to accelerate the dissolution of the thrombus. Endovascular devices have also been used adjunctively with chemical thrombolysis and fibrinolysis or primarily to treat a thrombus; however, distal access to a thrombus is limited due to the large size of available devices relative to small distal vessel diameters and due to the difficulty of maintaining proximal support of the access system that allows entry into the distal tortuous anatomy.

It would be desirable to provide an apparatus for and method of allowing an energy such as electromagnetic energy to be applied in close proximity to a distal thrombus to aid in the dissolution of the thrombus or aid in the localization of thrombolytic and fibrinolytic drugs to the thrombus.

The distal aspect of endovascular guide wires are frequently shaped by the user to achieve better navigability into the distal vascular anatomy, but conventional methods of shaping (e.g., rigid shaping mandrels) would impart trauma to elements that could be coupled to the guide wire, thereby causing device failure.

It would be desirable to provide a device for shaping the guide wire without imparting trauma to the guide wire that may cause device failure.

SUMMARY

One embodiment of the invention relates to a method of treating a thrombus. The method comprises providing a guide wire with an inductive element within a blood vessel to a location associated with the thrombus; and providing electromagnetic energy via the inductive element to the thrombus to cause thrombolysis.

Another embodiment relates to a catheter comprising a guide wire, and an inductive element disposed on a distal end of the guide wire. The inductive element of the guide wire receives an electric current and can have a diameter of less than 0.105 inches.

Another embodiment relates to a catheter comprising a guide wire, and an inductive element disposed on a distal end of both the guide wire and the catheter. The inductive element of the guide wire receives an electric current and can have a diameter of less than 0.105 inches. The inductive element of the catheter receives an electric current and can have a diameter of less than 0.131 inches.

Another embodiment relates to a catheter comprising a guide wire which can have a radius less than 0.020 inches, and a coil means for providing electromagnetic energy. The coil means is comprised of at least one or a multiplicity of conductive wires disposed on a distal end of the guide wire. The coil means can have a diameter of less than 0.040 inches. The conductive wire can have a diameter less than 0.020 inches.

According to another embodiment, the distal end of the guide wire can have an actuator wire or segment attached. An inductive element can surround the distal end of the guide wire and the actuator segment if incorporated. The actuator wire or segment can receive electric current independently or as part of a circuit with the inductor element. When the actuator wire receives electrical current, a conformational change may be imparted to induce mechanical energy at the distal end of the guide wire. The diameter of the actuator wire can be equal to or smaller than the overall diameter of the proximal portion of the guide wire and can have a diameter less than 0.105 inches.

According to further embodiments, a conductive wire may also maintain a circuit with actuator wires embedded in a catheter wall causing the catheter body to become more rigid and increase the proximal support of the access system due to conformational changes of the actuator wires when current is delivered. The diameter of the catheter based actuator wires can be overall comparable to the conductive wire of the catheter based inductor coil and can have a diameter less than 0.020 inches. The catheter based actuator wires can also be present independently of a distally oriented catheter based inductor element, and can also receive current independently when an inductor element is present.

Another embodiment relates to the method of shaping the guide wire used for treating a thrombus and is applied around the distal aspect of the guide wire and shaped manually by hand to curve the guide wire without causing external trauma to an inductive element and actuator segment attached to the guide wire. The shaping device retains the applied shape with the assistance of malleable wire incorporated into the wall of the shaper. Shaping of the guide wire can be assisted by:

1. heat (imparted by heating elements or steam); or
2. electrolytic or chemical treatment.

The heat and chemical reaction cause the guide wire to have the applied shape set into the guide wire, or retained by the guide wire after removal of the distal end of the guide wire from the shaping device.

Another embodiment relates to the use of radiopacity or radiopaque markers located at a distal end of the catheter. Yet another embodiment relates to the use of medications transported using an inductive element at the distal end of an insertion tube of a catheter, at a distal end of the guide wire, or at both the distal end of the insertion tube of the catheter and the distal end of the guide wire. Using coaxially inserted catheters with individual inductive elements allows for further sub-localization of the transported medication beyond what can be achieved with inductive elements located at the end of a single catheter and guide wire system.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

These and other features, aspects and advantages of the present invention will become apparent from the following description, appended claims, and the accompanying exemplary embodiments shown in the drawings, which are briefly described below.

DETAILED DESCRIPTION

Figure 1A:
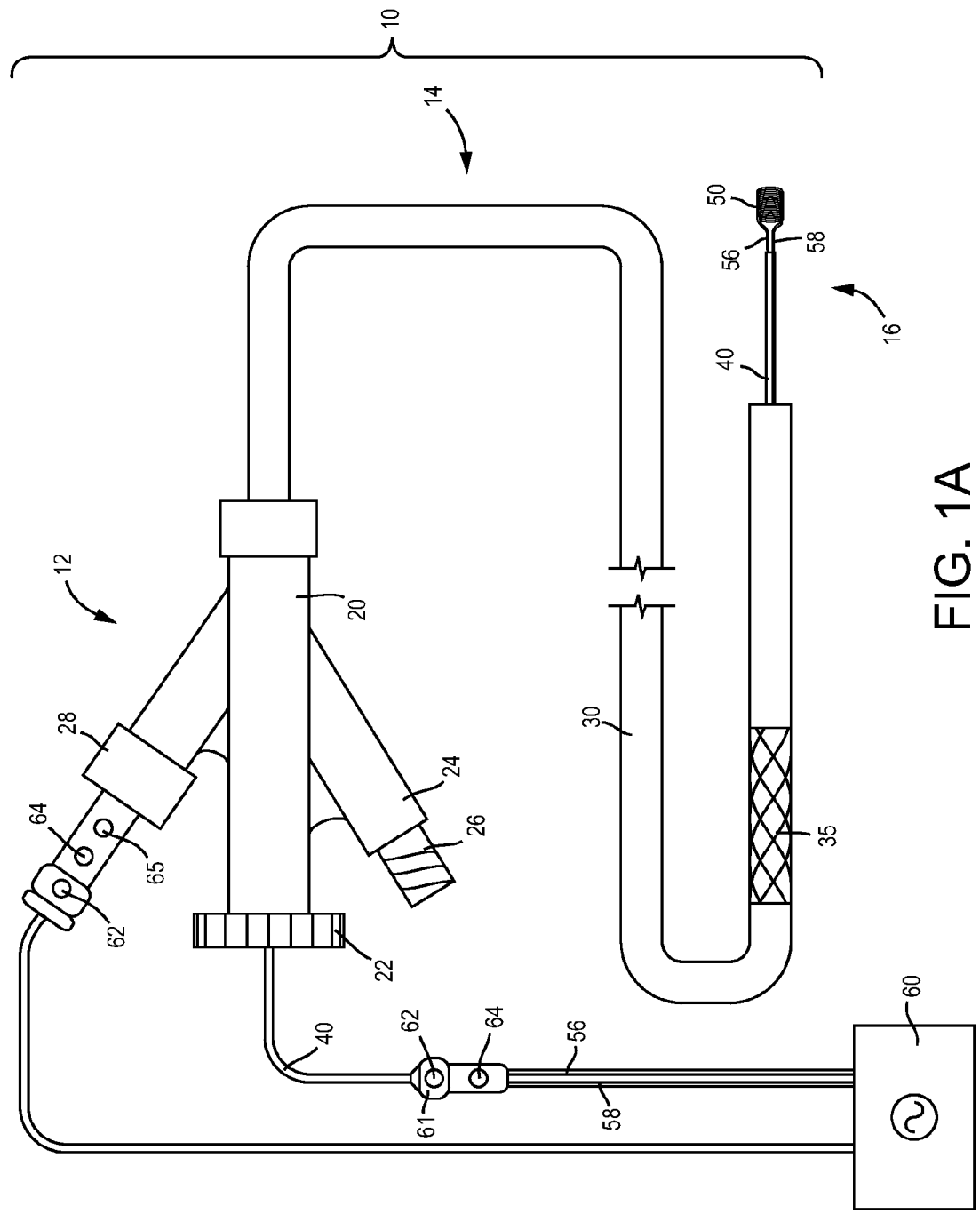
FIG. 1A is a side elevation view of a catheter system including an electromagnetic induction device according to an exemplary embodiment.

According to a preferred embodiment, a catheter device can be configured to facilitate the disruption and dissolution of a pathologic lesion (e.g., blood clot, thrombus, or other blockage) in a blood vessel by delivering electromagnetic energy, mechanical energy, or both electromagnetic energy and mechanical energy directly to the area of the pathologic lesion, (e.g., thrombosed vasculature). According to the preferred embodiment, the catheter device can also be configured to provide proximal support for distal localization. The catheter device can be used in procedures that prevent, for example, an ischemic stroke caused by reduced blood flow to the brain. The electromagnetic energy is preferably applied with an inductive element that is coupled to the end of a guide wire and catheter. By placing the electromagnetic coils on the end of a guide wire, the energy is able to be administered directly to the area of thrombus. By placing the electromagnetic coils on the end of the catheter, the energy assists in the preferential localization of medicated magnetic particles to the arterial territory with thrombosis. Intrinsic mechanical energy can be applied to the area of thrombus by the positioning an actuator in the distal end of the guide wire to produce a conformational change after electrical current is applied; variable currents could achieve fluctuating conformational changes. Proximal support of the system can be achieved by the incorporation and activation of actuator wires in the proximal catheter wall following the application of electrical current to make distal localization of a coaxially inserted smaller diameter catheter and the guide wire mechanisms easier. Due to the small size of such a medical device and the possibility of damaging the distal segment of the guide wire while trying to create a user specified shape, an external shaping system can be utilized to limit any damage that could be imparted by user induced shaping at the time the device is used. The use of an external shaping device limits the trauma imparted on the guide wire associated with conventional point-of-care shaping methods.

The inductive element is preferably formed by a single or multiple layers of looped magnet wire (e.g., insulated wire). Exogenous current is applied to the inductive element to generate the electromagnetic energy. Alternatively, an integrated circuit (e.g., spiral track disposed in a silicon substrate) or squirrel cage configuration could be used to provide conductors for generating the magnetic field. Stimulation energy can be of variable frequency and voltage to generate a variable amount of magnetic flux.

The inductive element may be used alone or with a variety of other treatments to better dissolve pathologic lesions (e.g., thrombi). For example, the inductive element can be used primarily or along with intravascular medicines such as thrombolytics and fibrinolytics (e.g., streptokinase, tissue plasminogen activators (tPA), etc.). As described by Gorczyńska (Physiol Chem Phys Med NMR. 1983; 15(6):459-68. and J Hyg Epidemiol Microbiol Immunol. 1988; 32(4):391-6.), electromagnet fields have been found to increase rates of fibrinolysis and dissolution of thrombus. Externally applied therapeutic electromagnetic fields with amplitudes comparable to cellular physiologic and molecular magnetic field levels have been described by Jacobson and Yamanashi (Physiol Chem Phys & Med NMR. 1994; 26: 287-97). Applying electromagnetic energy to the site of a thrombus may facilitate thrombolysis and fibrinolysis with or without intravascular administration of medication.

A microcatheter with an inductor or inductive element located at the distal end can serve as a proximal source of electromagnetic energy. The inductor produces an electromagnetic field to assist in the endovascular localization of intravenously or intra-arterially administered medicated ferromagnetic nanoparticles or microparticles. Localization of intravenously administered medicated ferromagnetic nanoparticles or microparticles using an exogenous electromagnetic source has been described by Ma et al. (Biomaterials. 2009 Jul. 30 (19):3343-51.). When used in conjunction with an inductor coil disposed on the end of a more distally oriented guide wire, further sub-localization of such medicated particles is possible into the distal vasculature and at the site of a distal thrombus. The use of coaxially inserted catheters with distally located inductors in addition to the guide wire based inductor can provide three or more orders of vascular subdivision localization of such medicated particles.

An actuator wire incorporated into the distal aspect of the guide wire will allow for a secondary conformation to be achieved after the guide wire is localized at the thrombus. This conformational change imparted by the administration of electrical current will deliver mechanical energy to the thrombus. The addition of mechanical energy to the electromagnetic energy (from the inductor coils) will help facilitate thrombolysis. By delivering a fluctuating level of electrical current through this segment, variable degrees of conformational change can be achieved and help macerate the thrombus.

The inductive element can also be used in conjunction with an aspiration system mediated through the proximally positioned catheter. The distally positioned inductor coils and actuator segment facilitate the dissolution and fragmentation of the thrombus, while negative pressure applied to the proximally oriented catheter serves as a means of aspirating the fragments for removal from the vasculature.

According to one embodiment, the quality of radiopacity or having radiopaque markers located at the distal end of the catheter (both with or without an induction element) and guide wire. Tantalum or metal/platinum markers can be embedded into the catheter wall or wire coating or within the inductive element. The markers can assist in ensuring safer and more accurate positioning of the device in the vasculature under radiographic guidance.

An external guide wire shaping apparatus allows for the precise atraumatic shaping of complex configurations onto the distal end of the guide wire. Conventional user imparted methods of shaping guide wires is performed by rubbing a shaping mandrel across the segment where user-defined shape is desired. This method could impart trauma to the inductor and actuator segments and cause them to become nonfunctional. According to a preferred embodiment, an externally applied shaper would cause little to no trauma, and hold the guide wire in the desired shape while the shape was set into the guide wire by a permanent method (heat, electrolytic, chemical, etc.).

Figure 1B:
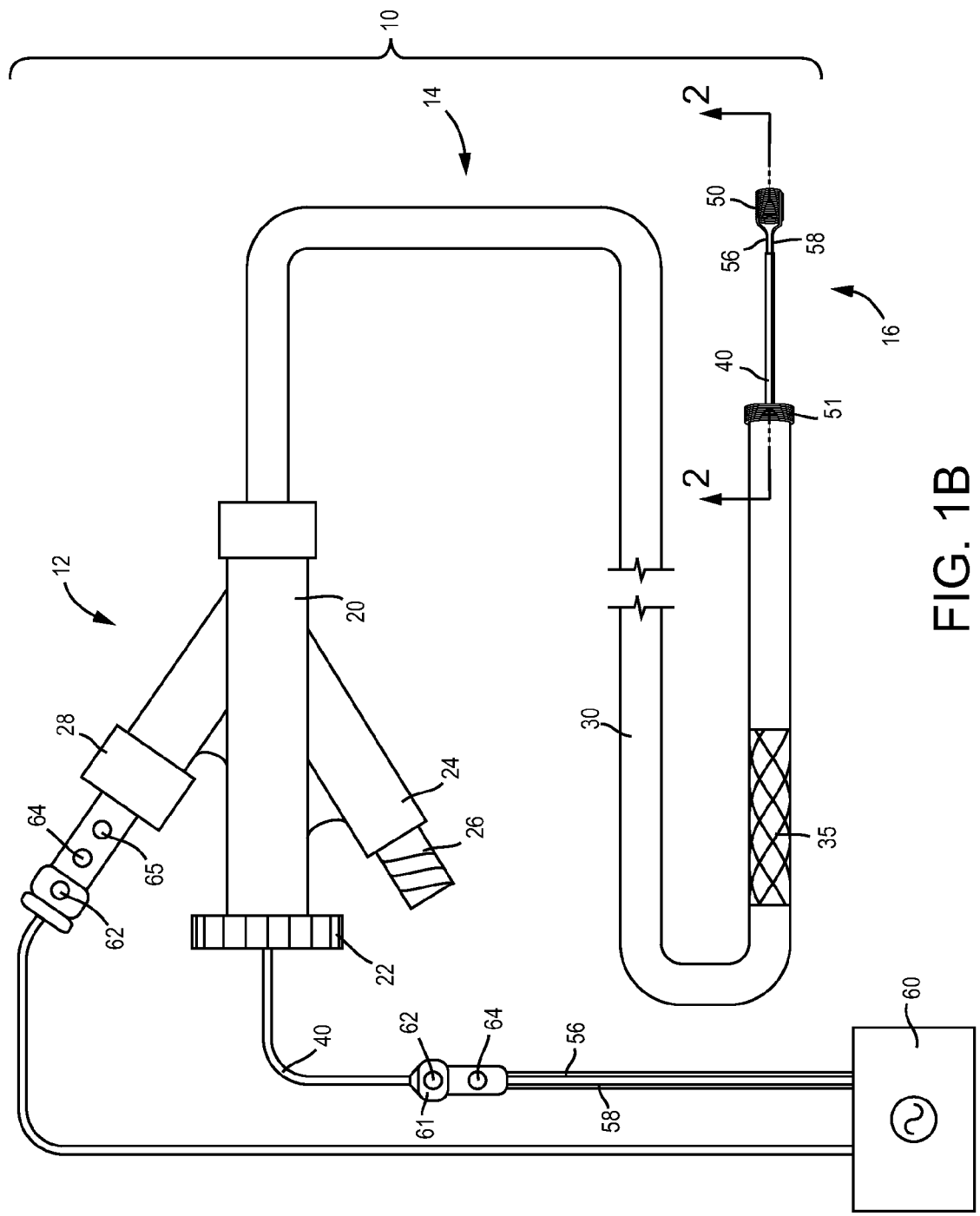
FIG. 1B is a side elevation view of a catheter system including an electromagnetic induction device, a second integrated electromagnetic induction device and actuated support braiding according to an exemplary embodiment.

Referring to FIGS. 1A and 1B, a catheter system 10 is shown according to an exemplary embodiment. Catheter system 10 is configured to deliver a fluid or a surgical instrument to an interior body cavity or blood vessel. For example, according to a preferred embodiment, catheter system 10 may be used to facilitate the dissolving of a thrombus with an electromagnetic field. Catheter system 10 comprises a base 20, an insertion tube 30, a guide wire 40, and an inductive element 50 that is introduced into the body with and through the insertion tube 30. Catheter system 10 has a proximal portion 12, an intermediate portion 14, and a distal portion 16. Inductive element 50 can be a coil of conductive wire and located on the distal end of guide wire 40. As shown in FIG. 1B, an inductive element 51 can be disposed on the terminal segment of distal portion 16 of insertion tube 30. Inductive element 50 can have a length from 1 to 30 cm; guide wire 40 can have a length of up to 320 cm. Inductive element 51 can have a length from 1 to 30 cm.

Proximal portion 12 comprises base 20 (e.g., manifold) with a rotating hemostatic valve (RHV) 22 through which guide wire 40 extends and allows medical personnel to manipulate guide wire 40 and magnetic induction device 50 (e.g., inductive element, inductive member, etc.) located at the distal end of guide wire 40. A second magnetic induction device or inductive element 51 (FIG. 1B) may be embedded in or placed on the surface of the terminal segment of distal portion 16 to deliver electromagnetic energy at a site more proximal than the inductive element 50 associated with guide wire 40. Distal portion 16 of insertion tube 30 may further include a reinforcing actuator segment 35 comprised of multiple actuator wires embedded in or on the surface of insertion tube 30. The length of segment 35 can be increased or decreased in accordance with application criteria.

Proximal portion 12 further includes an aspiration or infusion port 24 coupled to a luer assembly 26 through which fluids may be removed from or inserted into the body. For example, if catheter system 10 is a suction catheter, fluids and particles, such as from a dissolved thrombus, may be extracted from the body by aspiration from the port. According to other exemplary embodiments, port 24 may be used to introduce medicines such as antithrombotics and fibrinolytics (e.g., tissue plasminogen activators (tPA), etc.) into the blood vessel proximate to the thrombus. According to still other exemplary embodiments (FIG. 1B), port 24 may be used to introduce medicated ferromagnetic nanoparticles or microparticles into the blood vessel proximate to the thrombus to be localized distally towards the thrombus by inductive element 51 on the distal end of tube 30 and to be localized more distally at the thrombus by inductive element 50 on the distal end of guide wire 40.

Proximal portion 12 may have an alternative embodiment in which no rotating hemostatic valve (RHV) 22 is integrated onto the base 20. In such an embodiment, the base 20 terminates proximally as an infusion port 24 with a coupled luer assembly 26, rather than having port 24 extending off of the side of base 20. A separate rotating hemostatic valve or multi-port valve can be attached to the luer assembly 26 manually in a user defined configuration.

Intermediate portion 14 comprises an outer insertion tube 30 (e.g., guide tube, etc.), and a movable element such as guide wire 40 that is housed within insertion tube 30. Insertion tube 30 is a hollow member that is formed of a very flexible material, such as, silicone or a thermoplastic elastomer in single or multiple layers and woven with reinforcing braiding for variable support. Insertion tube 30 is configured to be able to be threaded through narrow passages such as blood vessels without damaging soft tissue. Insertion tube 30 provides a hollow passage through which a medical device or medicine may be delivered endovascularly or within a hollow organ.

Figure 1C:
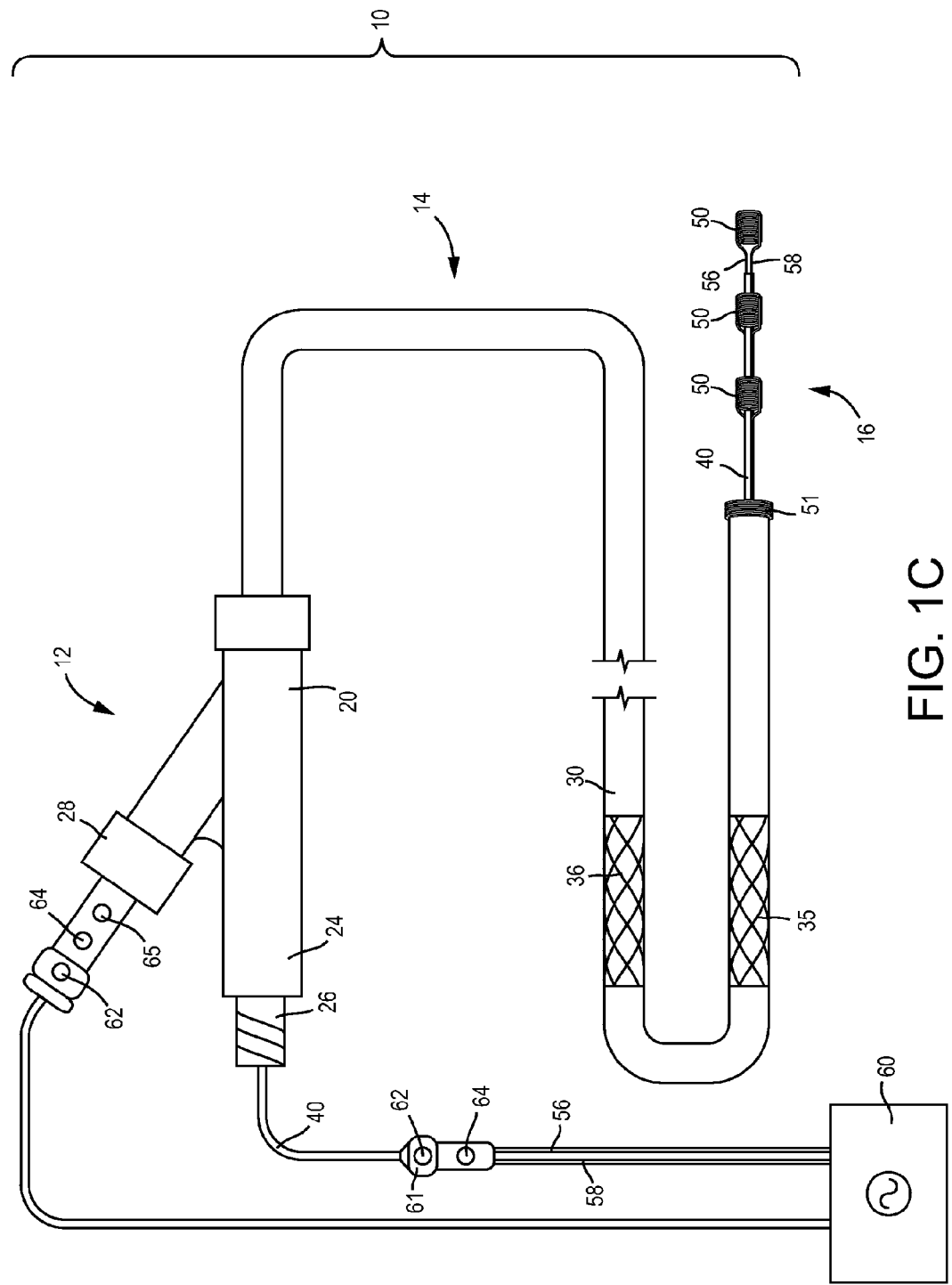
FIG. 1C is a side elevation view of a catheter system including tandem electromagnetic induction devices and a number of actuated support braidings according to an exemplary embodiment.

In an exemplary embodiment, insertion tube 30 includes a reinforcing actuator segment 35 formed of a conductive shape memory alloy (e.g., Nitinol, etc.). Other exemplary embodiments may not include a reinforcing actuator segment 35. An electrical current can be applied to the reinforcing actuator segment 35 to modulate the support or shape of insertion tube 30. According to one exemplary embodiment, a separate current may be supplied to reinforcing actuator segment 35 using separate conductors. According to another exemplary embodiment, electric current can be supplied using conductors or leads 56 and 58 associated with inductive element 51. Reinforcing actuator segment 35 may comprise a braided or woven structure, as shown in FIGS. 1A-B, or may comprise multiple actuator wires. Alternate actuator wire configurations are also possible. With reference to FIG. 1C, multiple actuator segments 35, 36 can be included. Although two segments 35 and 36 are shown, system 10 can include a greater number of segments 35 and 36 in one embodiment. The additional segments allow for further support or shaping of tube 30.

According to an exemplary embodiment, guide wire 40 coupled to inductive element 50 is introduced into insertion tube 30. Guide wire 40 is preferably an elongated member that facilitates the insertion and placement of insertion tube 30 within a body blood vessel. Guide wire 40 can be inserted through the lumen of a hollow needle that is inserted into the blood vessel. Once inserted, the needle is withdrawn and insertion tube 30 is fitted over guide wire 40. Guide wire 40 may also be introduced coaxially with insertion tube 30 through a vascular introducer sheath. Insertion tube 30 and guide wire 40 are then advanced through the blood vessel until the distal portion is proximate to the area of interest. To aid in the navigation of the blood vessel, guide wire 40 is generally flexible at the distal tip (e.g., proximate to inductive element 50) to allow guide wire 40 to follow a desired path and relatively stiff along the rest of its length to provide support for the catheter and resist unintentional bending during insertion and withdrawal. The distal aspect of guide wire 40 may be shapeable to improve the navigability within a vascular system by rotating the proximal end of guide wire 40. According to an exemplary embodiment, guide wire 40 has a diameter of between about 0.008 in. to 0.036 in, with a terminal segment diameter between 0.002 in. and 0.036 in. Smaller diameter distal portions may be formed, for example, by welding or otherwise bonding successively smaller diameter wires together.

Guide wire 40 locates inductive element 50 at the distal portion 16 of catheter system 10, proximate to an area of interest such as a thrombus. Guide wire 40 extends through RHV 22 at proximal portion 12, through insertion tube 30, to the distal portion 16. As discussed in more detail below, according to various exemplary embodiments, guide wire 40 may be part of a conductive path for inductive element 50 located at the terminal portion of guide wire 40 or may be insulated from inductive element 50. Guide wire 40 may be manipulated (e.g., extended, retracted, rotated, etc.) at the proximal portion 12 to effect a change in the position and/or orientation of inductive element 50 at the distal portion 16 of catheter system 10.

Inductive element 50 is configured to produce a localized electromagnetic field to stimulate the faster dissolution of the thrombus and localize medicated magnetic particles near the target lesion. Inductive element 50 is provided at the distal tip of guide wire 40 to allow a great degree of precision and accuracy in the location of inductive element 50. Guide wire 40 is typically less than (preferably approximately 75% of) the outer diameter of insertion tube 30. Guide wire 40 can be extended past the distal end of insertion tube 30, thereby extending inductive element 50 further into more distal narrow blood vessels. In this way, inductive element 50 can treat a thrombus in a narrow blood vessel that is inaccessible to insertion tube 30. According to one exemplary embodiment, inductive element 50 is configured to treat a thrombus located in a blood vessel with a diameter less than 30.0 mm. According to a preferred embodiment, inductive element 50 is configured to treat a thrombus located in a blood vessel with a diameter less than 5 mm. According to a particularly preferred embodiment, guide wire 40 mounted inductive element 50 is configured to treat a thrombus located in a blood vessel with a diameter less than 0.5 mm.

According to an exemplary embodiment, inductive element 50 comprises a plurality of loops or coils of an insulated, conductive member such as an insulated wire. Commonly known as "magnet wire", such an insulated wire comprises a conductive core material, such as a metal wire, that is coated in a thin film of varnish (i.e., an enamel). According to various exemplary embodiments, inductive element 50 may comprise a wire of a variety of metals or alloys commonly known in the art (e.g., copper, nickel, aluminum, steel, copper alloys, nickel alloys, silver, gold, platinum, copper or nickel plated with a precious metal, etc.). An additional exemplary embodiment comprises inductive element 50 of conductive nanoparticles oriented linearly into a wire. The wire is coated to prevent adjacent coils from short circuiting. According to a preferred embodiment, inductive element 50 is formed of a coated copper wire. Copper is desirable for its high conductivity.

Copper wire is commonly available in diameters as low as 0.00049 for 56 AWG (American wire gauge) wire. Coated wire has a larger diameter because of the insulating coating applied to the metal. According to an exemplary embodiment, the wire forming inductive element 50 has a diameter between 0.0165 in and 0.00049 in. According to a preferred embodiment, the wire forming inductive element 50 has a diameter between 0.00099 and 0.00049 in. According to a particularly preferred embodiment, the wire forming inductive element 50 has a diameter of 0.00099 in. (50 AWG) or 0.0020 in. (AWG 44).

The wire is wrapped in a series of turns (e.g., loops, coils, etc.) to form inductive element 50. Once coiled, inductive element may be coated again such as by being dipped in an insulating coating. According to an exemplary embodiment, the insulating coating material 44 (FIG. 8) may fill open loop 45 formed by the conductive wire, resulting in a solid inductive element at the distal end of guide wire 40. The coating further electrically insulates the conductive wire, reducing the likelihood of the wire contacting the tissue. Further, the additional coating increases the structural rigidity of inductive element 50, reducing the likelihood it will be deformed due to inadvertent contact when inserting guide wire 40 into the blood vessel or when contacting the thrombus. According to one exemplary embodiment, inductive element 50 is coated with a polymer such as polyethylene, polystyrene, polytetrafluoroethylene, polyamide, or silicone.

Figure 2A:
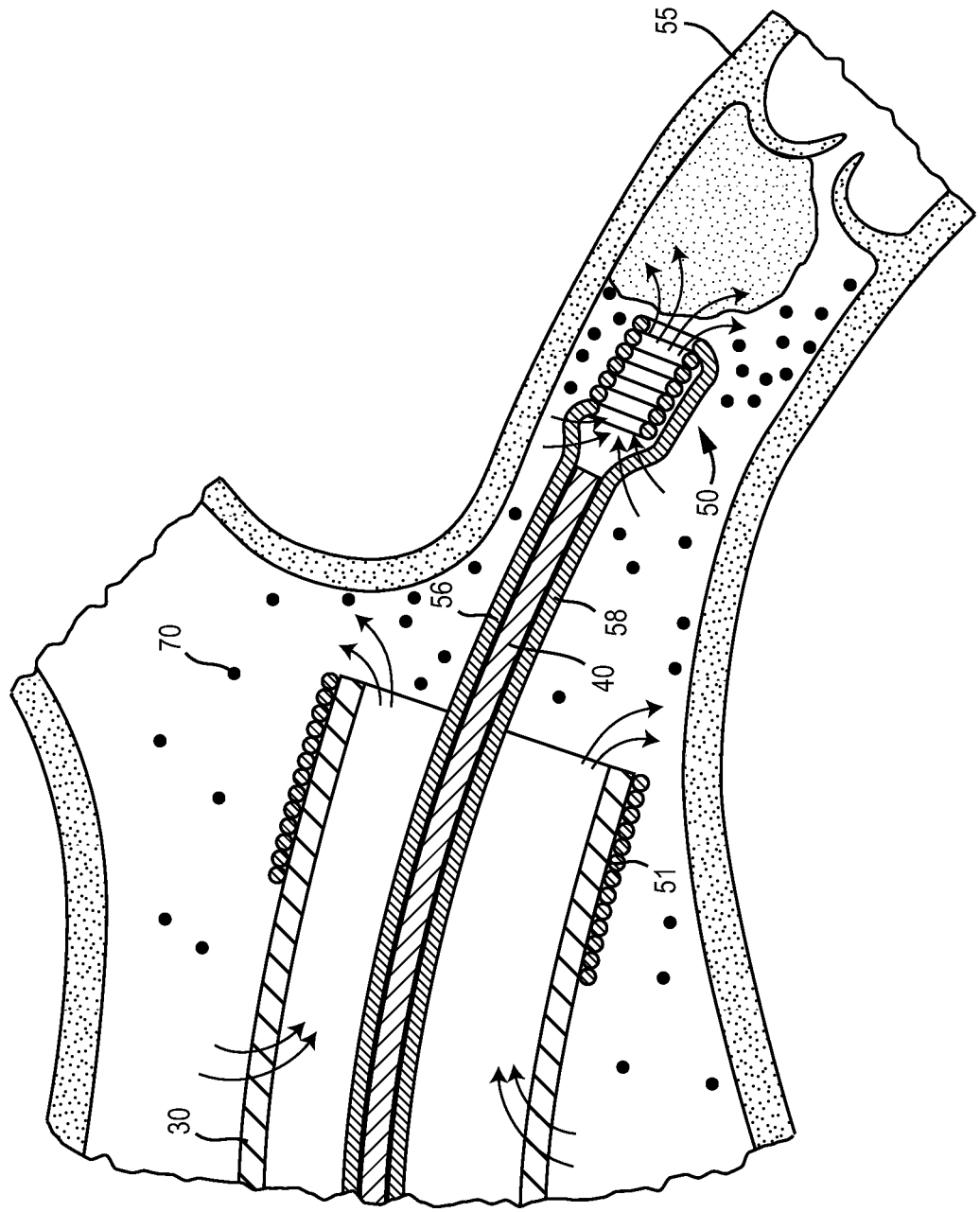
FIG. 2A is a cross sectional view of the distal end of the catheter system of FIG. 1 taken along line 2-2 showing the distal end providing treatment in a vessel according to another exemplary embodiment.
Figure 2B:
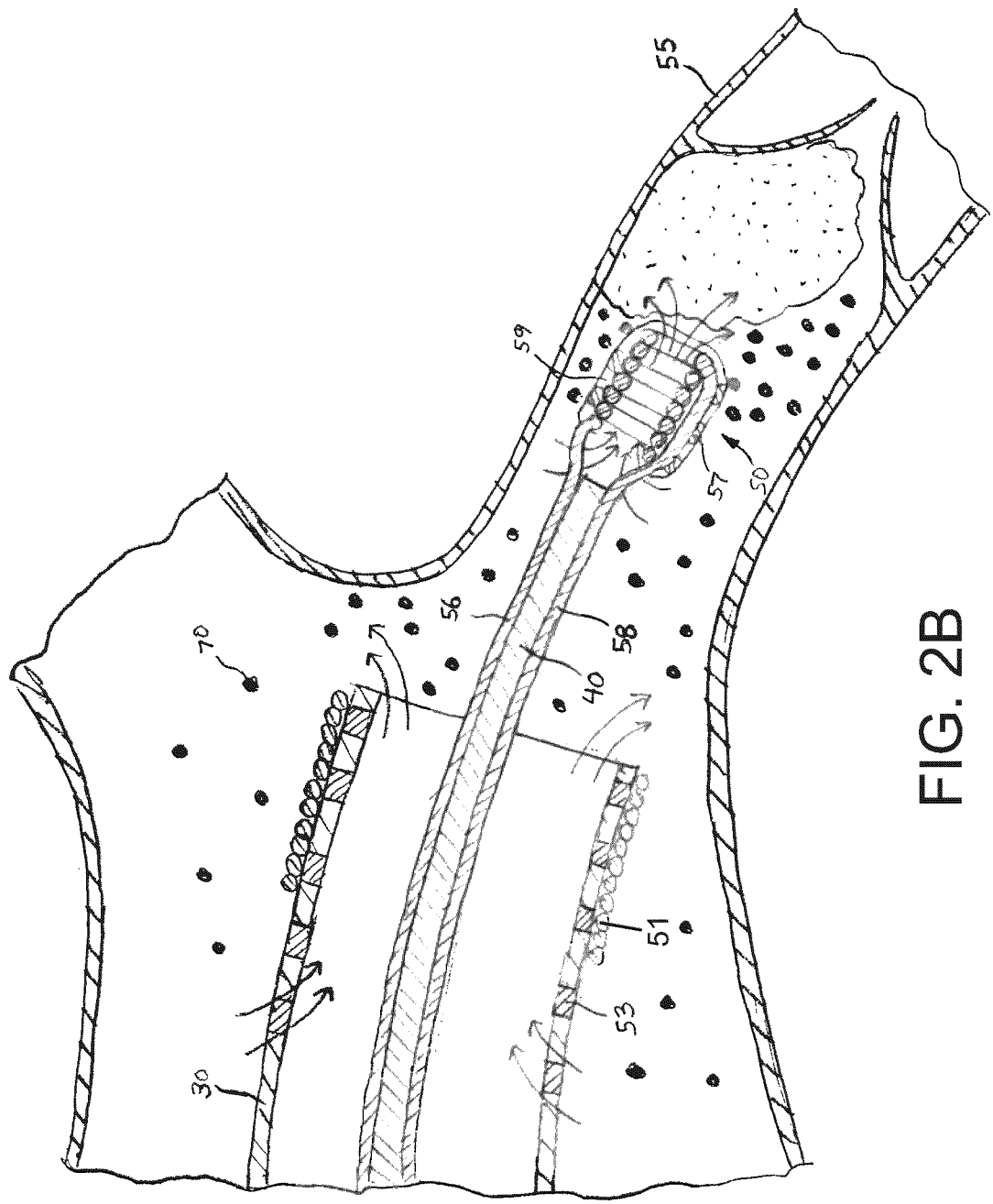
FIG. 2B is a cross sectional view of the distal end of the catheter system taken along lines 2-2 showing the distal end providing treatment in a vessel and including radiopaque markers according to yet another exemplary embodiment.
Figure 3A:
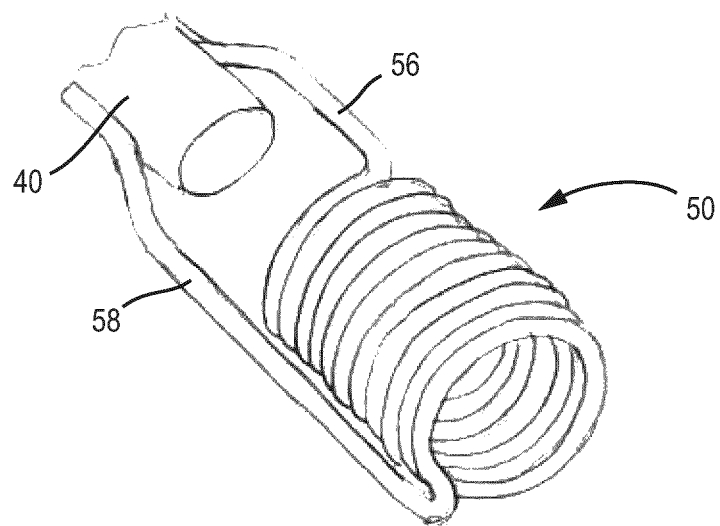
FIGS. 3A-B are isometric views of the distal end of the catheter according to exemplary embodiments.
Figure 3B:
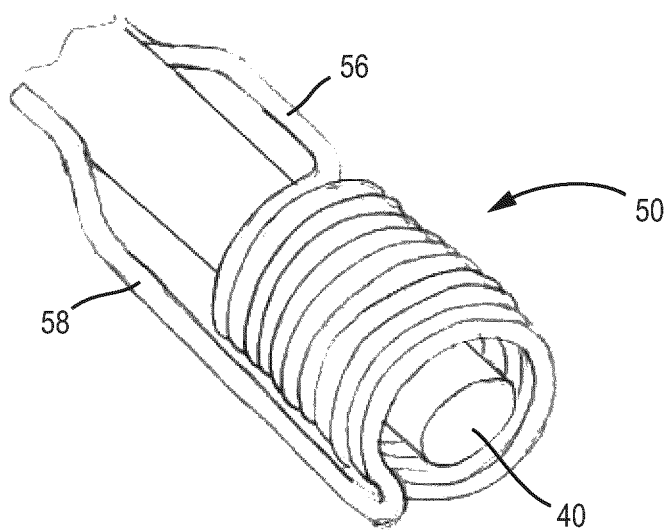

According to exemplary embodiments, as shown in FIGS. 1A-3, inductive element 50 is a generally cylindrical element. The loops forming inductive element 50 typically have a diameter less than 0.040 in. According to a preferred embodiment, the loops forming inductive element 50 have a diameter less than 0.035 in. According to a particularly preferred embodiment, the loops forming inductive element 50 have a diameter between 0.014 in. and 0.002 in. As shown in FIGS. 2A-B and 3, inductive element 50 may be formed of a single layer of loops. According to other exemplary embodiments, inductive element 50 may be formed by two or even more layers of nested loops. Additional exemplary embodiments of inductive element 50 can incorporate twisted, woven or braided wires to form the loops of the element.

Figure 4A:
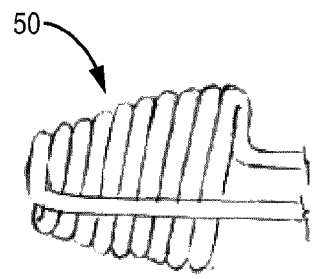
FIGS. 4A-D are side elevation views of the distal end of the catheter system of FIG. 1 according to various other exemplary embodiments.
Figure 4B:
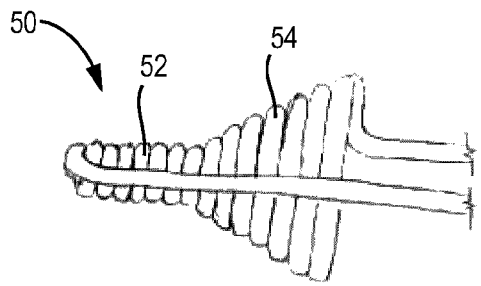
Figure 4C:
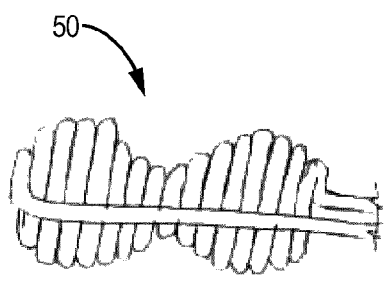
Figure 4D:
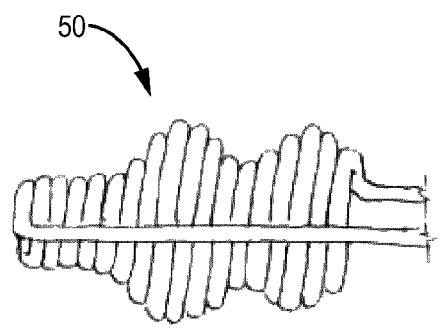

However, in other exemplary embodiments, inductive element 50 may be otherwise shaped to provide additional functionality. For example, as shown in FIG. 4A, inductive element 50 may be cone-shaped to facilitate the mechanical breaking up of the thrombus. Such an inductive element 50 comprises coils with diameters that increase in diameter as their distance from the distal tip increases. The increased diameter of the inductive element may also be formed by an increasing amount of nested loops as the overall diameter increases. As shown in FIG. 4B, according to another exemplary embodiment, inductive element 50 may comprise a first portion 52 proximate to the distal end of coils with a relatively small diameter and a second portion 54 with coils of a gradually increasing diameter. Referring now to FIGS. 4C and 4D, according to still other exemplary embodiments, inductive element 50 may have an undulating or wave-like profile such that the diameters of the loops increase and decrease several times along the length of inductive element 50. Such an inductive element 50 can be moved in and out along the length of the blood vessel in a sawing motion to help break up a thrombus or other blockage. In one embodiment, the terminal portion of guide wire 40 extends through inductive element 50 and inductive element 50 does not extend beyond the terminal portion. (See FIG. 3B.) Alternative shapes can be configured to also be used to break up clots using a twisting motion. After imparting structural integrity following coating inductive element 50 as described above, medical personnel may apply additional shape to the distal portion of inductive element 50. An additional exemplary embodiment has an overall configuration similar to that illustrated in FIG. 4B, but can have additional undulations or wave-like profile, similar to that seen in FIGS. 4C and 4D.

As generally shown in the FIGURES, inductive element 50 comprises a series of coils around a hollow core (e.g., a core of air, blood plasma, or another fluid that surrounds inductive element 50). According to one exemplary embodiment, inductive element 50 remains hollow within the coils, and can facilitate coring of the thrombus. However, according to other exemplary embodiments, inductive element 50 may comprise a core 42 (FIG. 8) formed from a material with a relatively high permeability such as ferrite. Including a high permeability core increases the inductance of inductive element 50. According to one exemplary embodiment, inductive element 50 is wrapped around the terminal portion of guide wire 40, such that guide wire 40 forms a solid core for inductive element 50.

In another alternative exemplary embodiment, an actuator segment or wire may comprise core 42 of the distally oriented inductive element 50 on guide wire 40, allowing for intrinsic mechanical action of inductive element 50 during a conformational change induced in the actuator segment following administration of electrical current through guide wire 40. The actuated segment comprising core 42 would receive current either independently or as part of a circuit with guide wire 40 oriented inductive element 50. In such an embodiment, if current is continuously applied across the actuator segment comprising the core 42, consistent conformational change and tension could be generated within the actuator segment. With consistent tension in the actuator segment, tracking the insertion tube 30 coaxially over guide wire 40 into more distally oriented tortuous vasculature could be less difficult.

Inductive element 51 coupled to insertion tube 30 of catheter system 10 can be composed of single or multiple nested layers of loops and may produce a magnetic field that is configured to direct or propel and concentrate small magnetic particles preferentially towards an area of interest in a vessel 55. Such particles may be, for example, medicated ferromagnetic nanoparticles or microparticles 70 (as shown in FIG. 2A). Such particles 70 can be further directed or propelled toward the thrombus in vessel 55 by element 50. Coaxially inserted catheters with individual distally oriented inductive element 51 provide a higher order of vascular sub-localization than achieved with a single catheter and guide wire alone.

With reference to FIG. 1A-C, inductive element 50 can be powered by an external power source 60 and is coupled to power source 60 by two electrical leads, such as, conductors or leads 56 and 58. According to one exemplary embodiment, as shown best in FIG. 1A, a single length of wire may be used to form a first electrical lead 56, inductive element 50, and a second electrical lead 58. Electrical leads 56 and 58 may run along the length of guide wire 40 and emerge out of RHV 22 along with guide wire 40 to be connected to a power source. Electrical leads 56 and 58 may be connected to an intermediate device such as a status light 62 (e.g., an LED) configured to indicate if inductive element 50 is being powered. A power switch 64 allows a user to control whether or not power is provided to inductive element 50. Switch 64 may be, for example, a normally open switch that is closed only when a user is depressing a button. Power switch 64 may be coupled to the proximal end of insertion tube 30 and/or may be provided on a handheld intermediary 61 coupled to guide wire 40. An additional switch 65 serves to modulate the current supplied to reinforcing actuator segment 35.

While electrical leads 56 and 58 are shown on generally opposite sides of guide wire 40 in FIG. 2A, according to other exemplary embodiments, electrical leads 56 and 58 may be otherwise arranged, such as on the same side of guide wire 40. Electrical leads to an inductive element 50 provided on insertion tube 30 may be arranged such that they form a circuit with corresponding electrical leads to an inductive element 50 coupled to guide wire 40. Electrical leads to inductive element 50 or 51 may also maintain a circuit with electrical leads coupled to actuator element in core 42 or reinforcing actuator segment 35 respectively. Alternatively, eight separate leads could be utilized to service elements 50 and 51, segment 35 and the actuator element in core 42.

Guide wire 40 is preferably formed of an electrically conductive material and may therefore be used as part of the conductive path for inductive element 50. Because of the nature of guide wire 40, many alternative arrangements for powering inductive element 50. For example, an inductive element 50 may comprise only a single electrical lead 56 coupled to guide wire 40, with guide wire acting as the second electrical lead. According to still another exemplary embodiment, guide wire 40 may include a first conducting member and a second coaxial conducting member and inductive element 50 may have no additional electrical leads. According to yet another exemplary embodiment, electrical leads 56 and 58 of inductive element 50 may be bonded together and form guide wire 40, eliminating the need for a separate member.

Power supply 60 provides an electrical current to inductive element 50 through electrical leads 56 and 58. Power supply 60 also provides an electrical current to reinforcing actuator segment 35. Power supply 60 is able to provide a direct current or a current with variable frequency and voltage as controlled by a user so that inductive element 50 can produce a variable magnetic flux for the treatment of the thrombus. In one embodiment, the frequency is between 2 Hz and 99 KHz.

According to an exemplary embodiment, inductive element 50 produces a magnetic flux between $5 \times 10E-13$ webers per square meter ($5 \times 10E-9$ maxwells per square centimeter) and 1 webers per square meter (30,000 maxwells per square centimeter). According to a preferred embodiment, inductive element 50 produces a magnetic flux of approximately $1 \times 10E-6$ webers per square meter (0.01 maxwells per square centimeter).

Figure 5:
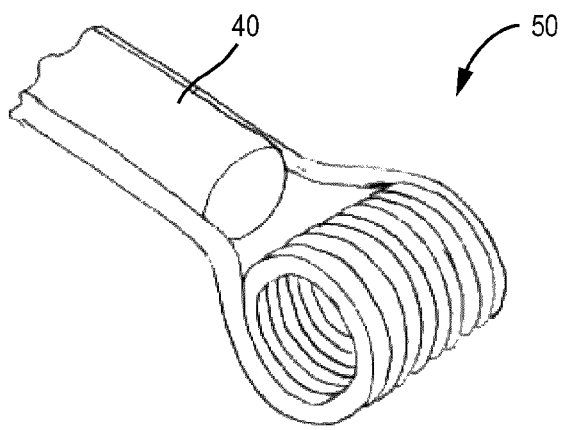
FIG. 5 is an isometric view of the distal end of the catheter according to another exemplary embodiment.

While inductive element 50 is shown in FIGS. 1A-4 as a coil with a longitudinal axis that is roughly parallel to the longitudinal axis of guide wire 50 and of the blood vessel, alternative orientations are possible in other exemplary embodiments. For example, as shown in FIG. 5, inductive element 50 may comprise a coil with a longitudinal axis that is roughly perpendicular to the longitudinal axis of guide wire 50 and of the blood vessel. A different orientation of inductive element 50 allows the electromagnetic field to therefore be oriented differently relative to the thrombus.

With reference to FIG. 2B, radiopaque markers 53 preferably are embedded or otherwise attached within or outside of insertion tube 30. Radiopaque markers 57 can also alternatively be attached or embedded within element 50. Markers 53 and 57 can be attached to elements 51 and 50, respectively, by embedding markers in 53 and 57 in a coating (such as coating 59 provided over element 50). Radiopaque markers 53 can also be embedded or otherwise attached within or outside of insertion tube 30 throughout the reinforcing actuator segment 35. Radiopaque markers 57 can also delineate the actuator element in core 42 disposed on the distal end of guide wire 40.

Marker 53 and 57 can include tantalum, metal/platinum or other radiopaque material. Marker 57 can also be attached to guide wire 40 (preferably at the distal end). Markers 53 and 57 can be utilized on a system 10 employed without elements 50 and 51. Markers 53 and 57 assist in ensuring safer and more accurate positioning of system 10 using radiographic guidance.

Markers 53 and 57 can have a variety of shapes. Preferably markers 53 and 57 are embodied as circular bands, rectangular-shaped members, or other shapes. Markers 53 and 57 can be spaced an equal distance apart. Markers 53 and 57 may also coalesce to appear as a single broad marked region. Ground or powdered radiopaque material can be bound onto or embedded into the regions of inductor elements 50 and 51, catheter actuator segment 35, and guide wire 40 actuator core 42, to appear as a broad marked segment under radiographic guidance.

With reference to FIG. 1C, an exemplary embodiment can include multiple inductive elements 50 disposed on guide wire 40. A series of multiple inductive elements 50 can be tandemly orientated on guide wire 40 to provide a higher order of particle sublocalization as compared to using guide wire 40 with a single element 50. In one embodiment, two inductive elements 50 may be utilized on guide wire 40 of catheter system 10. Alternatively, inductive elements 50 can number from 3 to 7. However, any number of elements 50 can be utilized.

Elements 50 are preferably positioned on wire 40 across a bifurcation point to direct traffic into the desired vascular pedicle in one embodiment. The size of elements 50 can be progressively smaller (e.g., smaller diameters) as the distal end of guide wire 40 is approached. Alternatively, elements 50 can be the same size and have the same diameter. In one embodiment, elements 50 are located on the last 60 cm or less of the distal end of guide wire 40. In one embodiment, elements 50 can be separated by a distance of from 1 to 20 cm.

Each element 50 can be powered by its own pair of conductors or leads 56, 58 to allow individual electric control of each of element 50. In one embodiment, more precise sublocalization concentration of a pharmacological agents via medicated ferromagnetic particles can be achieved by separately controlling elements 50. Alternatively, elements 50 can be controlled by the same wires or leads 56,58, and can be connected in series or in parallel. Various signals can be provided to elements 50 that provide pulsing or other modulations to improve sublocalization of the pharmacological agent. For example, synchronized pulses or other timed electrical signals can drive medicated ferromagnetic particles in a particular direction.

Use of multiple elements 50 can be utilized for thrombolysis, as in stroke or DVT/PE, or any condition where sublocalization concentration of pharmacological agents is desired, such as with endovascular treatment of malignancy or vascular malformations. Epistaxis 15 can be treated with embolization when refractory using catheter system 10 of FIGS. 1A-C.

According to one application, catheter system 10 with tandem elements 50 could be left in the vascular for an extended period of time allowing for longer periods of treatment. Smaller configurations (preferably the smallest possible) are utilized for elements 50 in this embodiment to reduce the risk of thrombogenicity. In addition, such a configuration can allow for more ambulatory applications. A single conductor 40 with two or more elements 50 can be used instead of catheter system 10 shown in FIGS. 1A-C. This embodiment allows sub localization using multiple elements 50 without requiring tube 30 with element 51. Accordingly, in one embodiment, the functionality of system 10 described with reference to FIG. 1B can be achieved through the use of tandem elements 50 on wire 40.

Element 50 can be a hollow core element having a diameter sufficient to pass element 50 over a microwire. In such an embodiment, tandem positioning of several elements 50 can be achieved over the microwire by introducing several elements 50 over the single microwire. In such an embodiment, the microwire can be placed in the vasculature, and elements 50 on guide wire 40 can be slid along the microwire. Elements 50 can be placed for optimal sublocalization concentration of pharmacological agent as discussed above to disrupt a thrombus or pathological lesion. Elements 50 can be disposed on individual guide wires 40 or on a single guide wire 40 in this embodiment.

Figure 6:
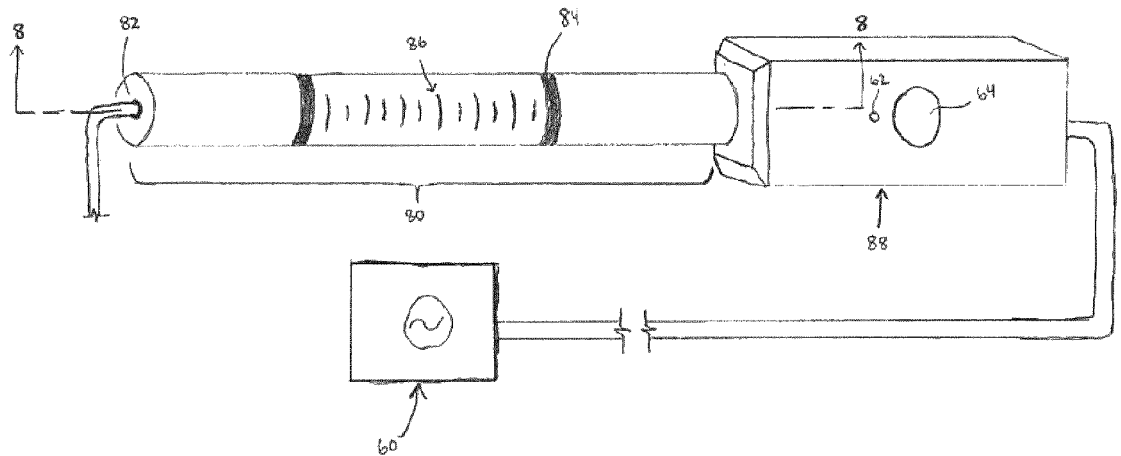
FIG. 6 is an isometric view of an atraumatic guide wire shaping device according to an exemplary embodiment, including a shaping segment, external markings to indicate guide wire positioning, an electrical power supply and a more distally oriented handle with activation button.

With reference to FIG. 6, an exemplary embodiment, according to an externally applied atraumatic shaping device 80 assists in the formation of user defined complex shapes to the distal aspect of guide wire 40. Shaping device 80 is configured to shape guide wire 40 to achieve navigability into distal vascular anatomy without imparting trauma to guide wire 40 that may cause device failure. As illustrated in FIGS. 6-8, guide wire 40 can be inserted within shaping device 80 through an entry port 82 to a depth that is indicated on the surface of shaping device 80 by a marker band 84. Additional length measure markings 86 are present on the surface of shaping device 80 to allow a higher precision of user defined shaping of guide wire 40. According to an exemplary embodiment, shaping device 80 has a handle 88 opposite entry port 82. Handle 88 includes an integrated power switch 64 and status light 62. The diameter of shaping device 80 is preferably two or more times the diameter of wire 40.

Figure 7A:
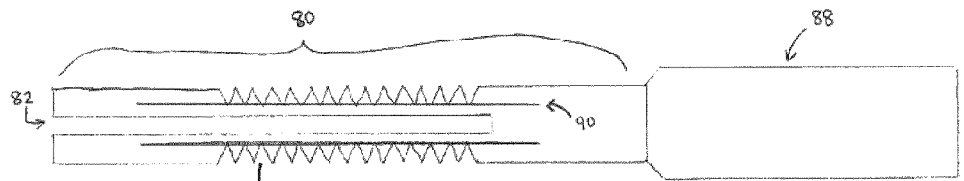
FIG. 7A is a cross sectional view of an atraumatic guide wire shaping device, including a serrated portion according to an additional exemplary embodiment, showing the shaping segment and the distally oriented handle.
Figure 7B:
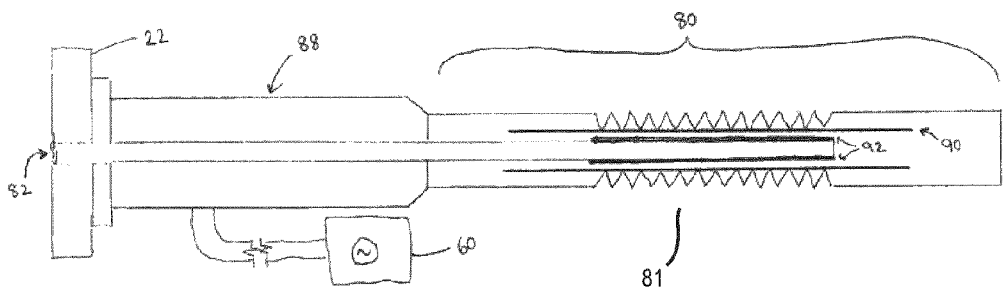
FIG. 7B is a cross sectional view of an atraumatic guide wire shaping device, including a serrated portion according to yet another exemplary embodiment, showing a shaping segment and a proximally oriented handle.
Figure 8:
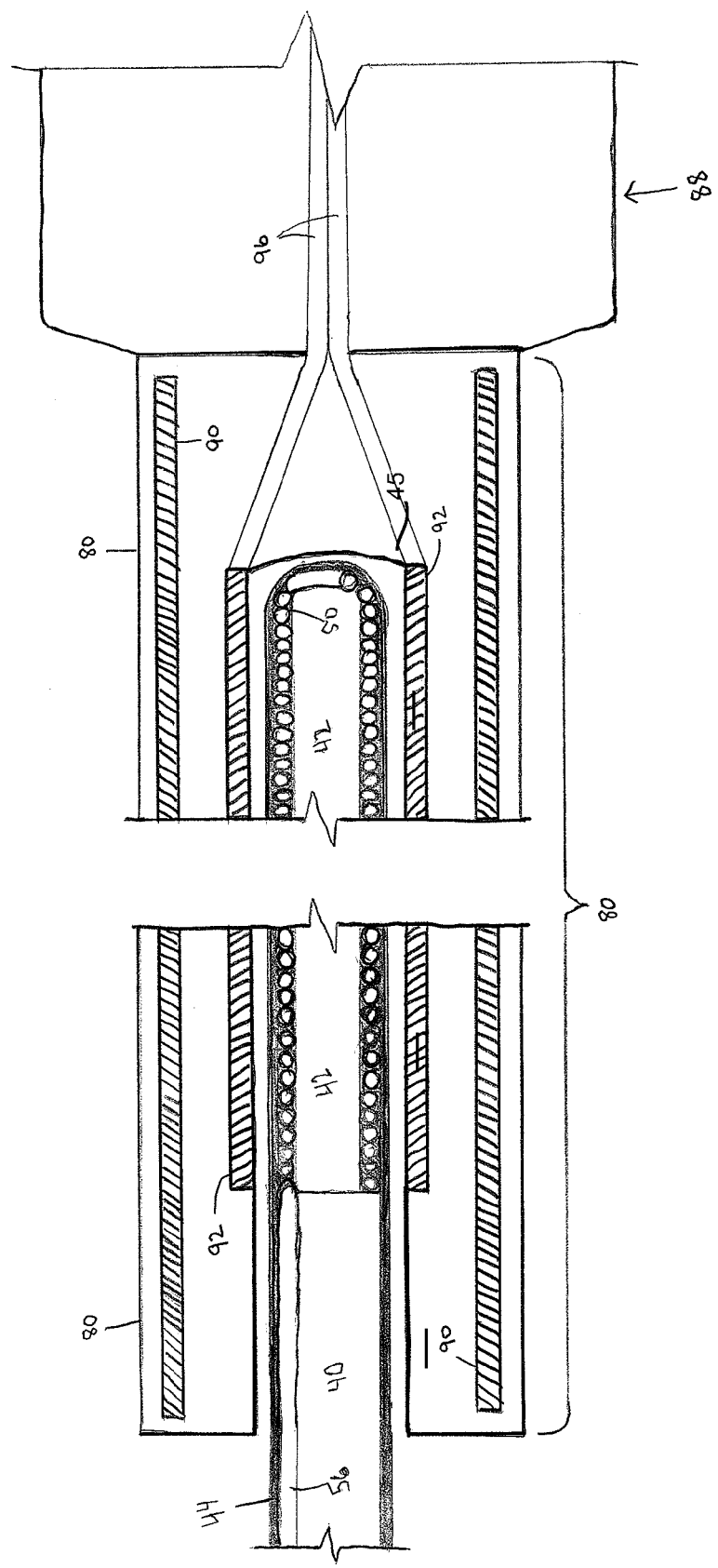
FIG. 8 is a cross sectional view of the atraumatic guide wire shaping device of FIG. 6 taken along line 8-8, including a guide wire inserted inside the shaping device that has a distally oriented electromagnetic inductor device and actuator segment according to an exemplary embodiment.

Referring to FIGS. 7A-B malleable shape retaining wire 90 is preferably embedded within shaping device 80 to maintain the user defined shape. According to an exemplary embodiment, malleable shape retaining wire 90 can be made of commonly known malleable wire (e.g., stainless steel, copper, etc.). Within shaping device 80, single or multiple malleable shape retaining wires 90 are oriented longitudinally within shaping device 80 and positioned radially around the hollow inner core, which houses the guide wire 40. According to an additional exemplary embodiment, contact electrodes 92 are positioned near the inner surface of the hollow core, as illustrated in FIGS. 7B and 8. Contact electrodes 92 are oriented longitudinally along shaping device 80 and radially around the inner surface of the inner core, adjacent to guide wire 40 when positioned inside shaping device 80. Contact electrodes 92 can receive electrical current through electrical leads 96. According to the exemplary embodiment, electrical leads 96 receive power from power source 60.

Following definition of a preferred user defined shape by manually positioning the shaping device 80 and malleable shape retaining wire 90, setting the shape into the guide wire 40 is performed by activating the contact electrodes 92 by depressing the power switch 64. According to an exemplary embodiment, contact electrodes 92 are formed of heating elements for heat setting a permanent change in the shape of the distal end of guide wire 40. An alternative embodiment allows for contact electrodes 92 to induce an electrolytic or electrochemical reaction at the surface of guide wire 40 when activated by depressing power switch 64. A further exemplary embodiment does not have contact electrodes 92, but otherwise functions similarly as the other embodiments for user definition of the guide wire shape. In such an embodiment, the application of externally delivered heat or steaming is used to retain or set the user defined shape in guide wire 40. The shape of the guide wire 40 may also be set by temporarily immersing the shaping device into a chemical solvent (e.g., Dimethyl sulfoxide) to cause a permanent conversion of the configuration of guide wire 40.

In an alternate exemplary embodiment, handle 88 can be located proximally to entry port 82 of shaping device 80 and can incorporate entry port 82, as illustrated in FIG. 7B. In such an embodiment with a proximally oriented handle 88, a rotating hemostatic valve (RHV) 22 can be positioned to secure guide wire 40 at the depth specified by surface marker band 84.

The surface configuration and profile of shaping device 80 can be variable. According to one exemplary embodiment, illustrated in FIG. 6, shaping device 80 may have a smooth surface configuration. According to another exemplary embodiment, illustrated in FIGS. 7A-B, shaping device 80 may have a surface 81 with a serrated type of profile. According to exemplary embodiments with a serrated surface configuration, larger amounts of user defined bending (e.g., at a specific curvature and angle) can be imparted on guide wire 40 due to a lack of intervening material between serrations, as is present in an embodiment with a smooth surface configuration. In a preferred embodiment, the size and shape of the serrations predefine a specific bending angle, such that the user is able to precisely define the shape of guide wire 40.

In the preferred embodiments already described, and with reference to FIGS. 1A-B and 8, activation of core actuator segment 42 (FIG. 8) and reinforcing actuator segment 35 (FIGS. 1A-B can be through energy imparted through electrical current. Alternatively, with reference to (FIGS. 1A and B and 9A), core actuator segment 42 can be activated through coupled mechanical energy delivered directly by applying manual tension or pressure onto the proximal aspect of core wire 43 situated within a hypotube 41 (FIG. 9A) that serves as an outer body for guide wire 40. Actuator segment 42 can be configured as a straight wire or as a more complex shape, such as a coil or zig-zig pattern. Additionally, activation of tension within insertion tube 30 at reinforcing actuator segment 35 can be achieved through administration of mechanical energy by applying manual tension via a sliding or screw mechanism onto coaxially oriented cords or wires 36 within the wall of insertion tube 30 (FIG. 9B). With reference to FIG. 9B, such cords or wires 36 can be a pair or multiple pairs oriented opposite each other, so as to limit excessive turning, bending, ovalizing, or twisting of insertion tube 30 across the actuated segment 35 (FIG. 1A) to provide increased support uniformly. Mechanical energy transmitted to both core actuator segment 42 and reinforcing actuator segment 35 would originate at the proximate ends of guide wire 40 and insertion tube 30 by user controlled manipulation of the mechanical actuation coupling 66, providing variable axial tensions and distal mechanical action.

Figure 9A:
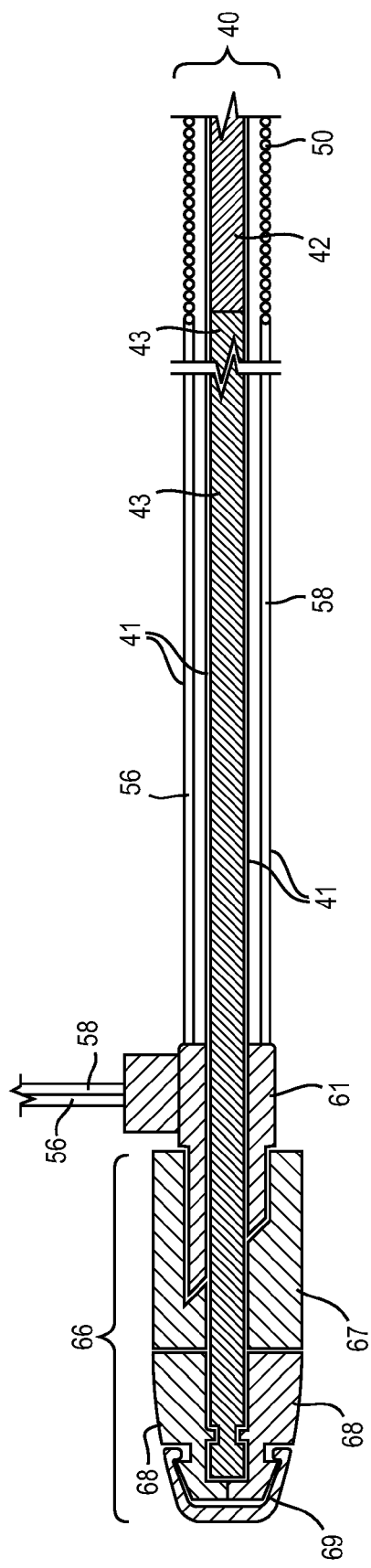
FIG. 9A is a cross sectional view of a guide wire system including a mechanically activated core actuator device in accordance with another exemplary embodiment.
Figure 9B:
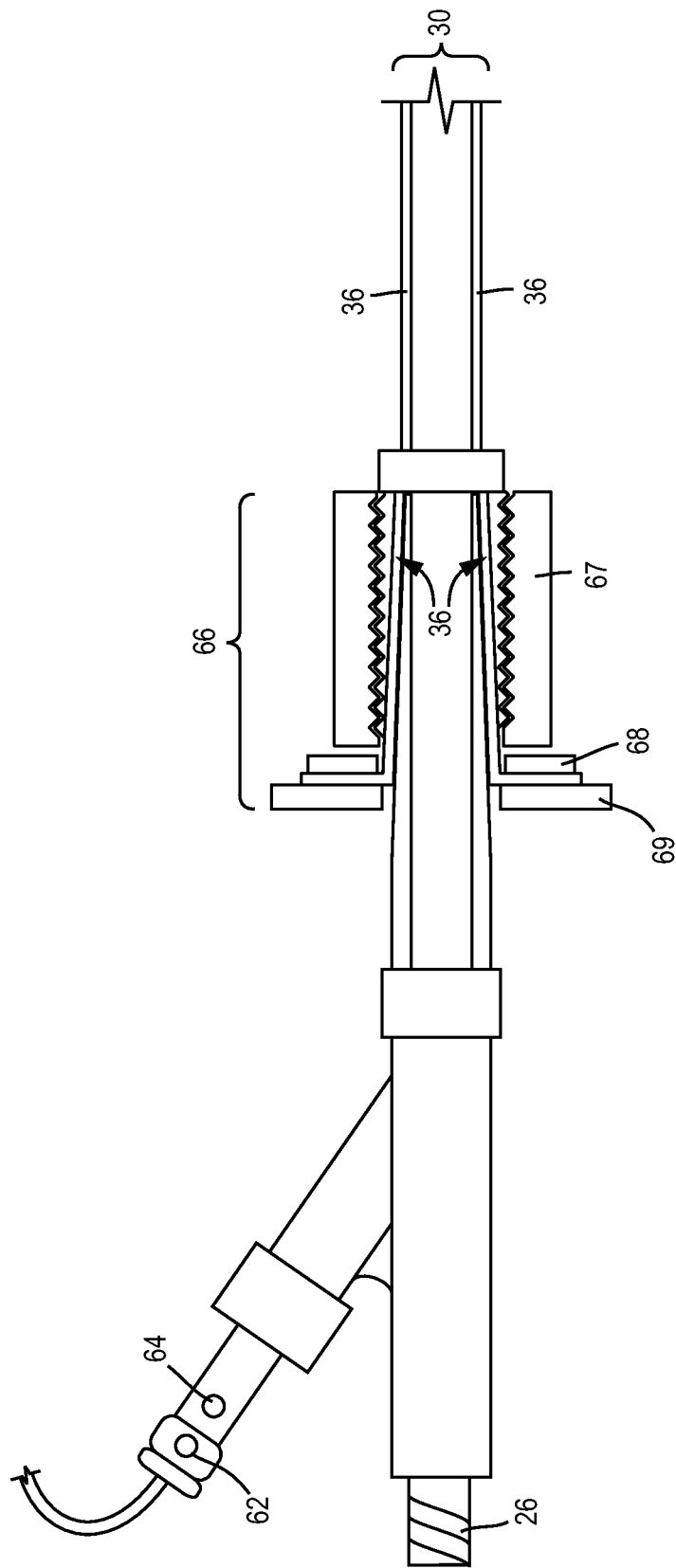
FIG. 9B is a sideview of a handle portion of a catheter system in accordance with still another exemplary embodiment with a mechanically activated support segment.

FIG. 9A represents a preferred embodiment capable of providing mechanical actuation of guide wire 40 by means of twisting activation component 67, causing an outward tension on core wire 43 which is secured by capping components 68 and 69, and coupled distally to actuator segment 42. An alternative embodiment can produce positive pressure for the mechanical energy within the actuator segment 42 by incorporating a spring-loaded plunger as activation component 67, rather than the twisting component depicted in FIG. 9A. FIG. 9B represents the proximal aspect of insertion tube 30 with an alternative embodiment capable of providing mechanical energy for activation of the reinforcing actuator segment 35. Cords or wires 36 are secured proximally by capping components 68 and 69; screwing of activation component 67 can cause an outward tension onto the capping components 68 and 69. An alternative embodiment can incorporate a sliding mechanism as activation segment 67 to provide tension into the coaxial wires 36, and in turn the reinforcing actuator segment 35.

Although stroke and thrombus treatment is the primary field of application for the described embodiments, additional pathological lesions may benefit from use with the exemplary embodiments described above with reference to FIGS. 1A-9B. The use of thrombolytic medicated ferromagnetic particles 70 can serve as an example of how the electromagnetic induction coil 50 could be of use in fields unrelated to the treatment of thrombus. If the medicated particles 70 contained chemotherapeutic medication, and are introduced either intravenously or intra-arterially within a feeding arterial pedicle for a tumor, a higher relative concentration of medication may be achieved within the index territory for the malignancy. Lower doses of intravenous medication may be possible while maintaining target tissue therapeutic concentrations by sublocalizing the medication using the inductor 50 positioned within the respective arterial tree; this would lead to less systemic side effects of the chemotherapy.

Although the atraumatic shaping device 80 has been primarily described as a shaping tool for guide wire 40, in an alternative embodiment, the lumen of shaping device 80 is capable of introducing the distal aspect of insertion tube 30 where induction element 50 would typically be disposed, with or without a mandrel positioned within the lumen of insertion tube 30. Using similar methods applied for shaping guide wire 40 with the use of atraumatic shaping device 80, user defined shape could be imparted to the distal aspect of insertion tube 30.

The construction and arrangement of the elements of the medical device as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited herein. For example, elements shown as integrally formed may be constructed of multiple parts or elements, the position of elements may be reversed or otherwise varied, and the nature or number of discrete elements or positions may be altered or varied. It should be noted that the elements and/or assemblies of the system may be constructed from any of a wide variety of materials that provide sufficient strength, durability, or biocompatibility. Other substitutions, modifications, changes and omissions may be made in the design, operating conditions and arrangement of the preferred and other exemplary embodiments and medical procedures without departing from the scope of the present invention.

What is claimed is:

1. A catheter, comprising:
    a hollow tube for insertion into a hollow organ or blood vessel;
    a guide wire;
    a first inductive element located at a terminal end of the guide wire, the first inductive element receiving an electrical current and having a diameter of less than 0.105 inches;
    a second inductive element embedded in or placed on a surface of a terminal segment of a distal portion of the hollow tube, the second inductive element receiving an electrical current; and
    an actuator comprising:
        an actuator segment comprising a core of the first inductive element; and
        a core wire disposed within the hollow tube and operably coupled to the actuator segment;
    wherein the actuator undergoes conformational change to increase the structural integrity of the catheter in response to an electrical current administered to the actuator through the guide wire; and
    wherein the actuator undergoes conformational change to increase the structural integrity of the catheter in response to mechanical tension applied to the core wire.

2. The catheter of claim 1, further comprising one or more additional inductive elements disposed on and tandemly oriented on the terminal end of the guide wire, wherein each of the first inductive element, the second inductive element, and the one or more additional inductive elements is powered by its own pair of leads to allow individual electric control of each inductive element, and wherein precise sublocalization concentration of medicated ferromagnetic particles can be achieved by separately controlling the inductive elements.

3. The catheter of claim 1, wherein the first inductive element is spiral or cone shaped or has a wave-like profile or is cylindrical having a radius of less than 0.0655 inches.

4. The catheter of claim 1, wherein the first inductive element is a coil, the coil being coated in an insulative material.

5. The catheter of claim 1, wherein the catheter is an aspirating catheter.

6. The catheter of claim 1, further comprising a mechanical actuation coupling operatively coupled to a proximate end of the guide wire, and at least one pair of coaxially oriented wires disposed within the hollow tube, wherein the at least one pair of coaxially oriented wires are coupled to the mechanical actuation coupling and a distal end of the guide wire; wherein user controlled manipulation of the mechanical actuation coupling is configured to provide variable axial tensions and distal mechanical action of the guide wire.

7. A method of treating a pathologic lesion using the catheter of claim 1, the method comprising:
    providing the catheter within a blood vessel to a location associated with the pathologic lesion; and
    providing electromagnetic energy via the first inductive element to the pathologic lesion.

8. The method of claim 7, wherein the first inductive element is a coil, the coil being coated in an insulative material, and wherein the insulative material provides additional support and integrity to the coil.

9. The method of claim 7, further comprising: applying a consistent electrical current to the actuator and applying a consistent mechanical tension to the actuator, wherein the actuator undergoes consistent conformational change in response to the consistent electrical current and the consistent mechanical tension.

10. The method of claim 7, further comprising:
    applying a variable electrical current to the actuator and a variable mechanical tension to the actuator, wherein the actuator undergoes variable conformational change in response to the variable electrical current and the variable mechanical tension; wherein the variable conformational change causes the catheter to macerate the pathologic lesion.

11. The method of claim 7, further comprising:
    introducing a drug comprising medicated magnetic particles to the location;
    localizing the drug distally towards the pathologic lesion by applying an electrical current to the second inductive element; and
    sublocalizing the drug more distally within a vascular subdivision by applying an electrical current to the first inductive element.

12. The method of claim 11, wherein the drug is provided as coated ferromagnetic particles.

13. The method of claim 7, further comprising providing electromagnetic energy to or within a thrombus, wherein the pathologic lesion is the thrombus.

14. The method of claim 7, wherein the hollow tube further comprises a variable tension actuator segment coupled to actuator wires, the method further comprising: applying an electrical current to the actuator segment via the actuator wires to modulate support of the hollow tube to allow further distal access of the guide wire and the first inductive element mounted on the guide wire.

15. A method of treating a pathological lesion using the catheter of claim 1, the method comprising:
   providing the catheter within a blood vessel to a location associated with the pathological lesion; and
   providing electromagnetic and/or mechanical energy via the first inductive element to the lesion, the mechanical energy being distal mechanical action or variable axial tensions.

* * * * *